Oct. 23, 1934. J. H. NICOLAS Plant Pat. 109
ROSE
Filed Jan. 3, 1934
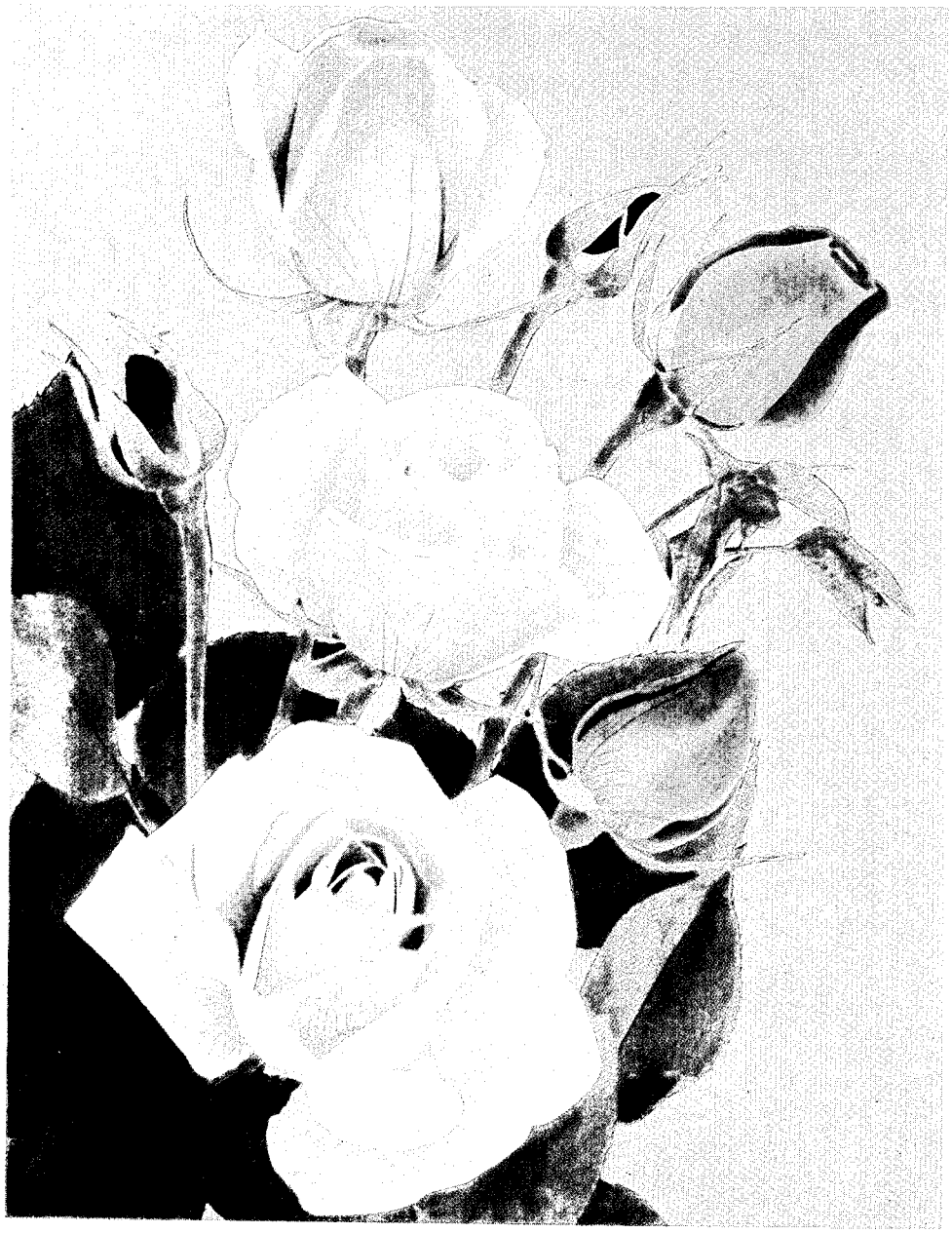
Inventor
J. H. Nicolas
By Robb & Robb
Attorneys Patented Oct. 23, 1934

Plant Pat. 109

UNITED STATES PATENT OFFICE

109

ROSE

Jean H. Nicolas, Newark, N. Y., assignor to Jackson & Perkins Company, Newark, N. Y.

Application January 3, 1934, Serial No. 705,157

1 Claim. (Cl. 47—61)

The present invention relates to a new and distinct variety of rose plant, the result of definite breeding efforts having as their primary objective the production of a new color in rose flowers.

This new rose seedling issued from crosses of hybrids of four distinct and unrelated species, *Rosa centifolia, Rosa borbonica, Rosa indica odoratissima* and *Rosa foetida lutea,* and is the direct result of crossing the hybrid tea Charles P. Kilham and a seedling of Ophelia crossed with Souvenir de Claudius Pernet.

The color of this new rose is a new departure in roses, said color being a chestnut red in the bud and half-open bloom, gradually changing to carrot red with orange suffusion in the full blown flower, finishing satiny coral. The flower is lasting and the evolution of color is very slow. This is the primary feature of distinctness of this new variety of rose. The color standard upon which the foregoing is based in the Gravereaux color system in "The Rose Manual" pages 259 to 264, by J. H. Nicolas.

A further distinct characteristic of this rose resides in the unusual profusion and continuity of bloom which are in general much in excess of those characteristics in the existing varieties of garden roses. Established plants average some seventy blooms in a season.

This plant can be used for forcing for the cut flower market and as such is considered a most valuable and novel addition to the florist industry.

The following is a detailed description of this rose plant and flower, which plant has been asexually reproduced and in which the characteristics thereof are found to be permanently fixed:—

Parentage:—
Seedling.
*Seed parent.*—Charles P. Kilham.
*Pollen parent.*—Seedling of Ophelia crossed with Souvenir de Claudius Pernet.
Classification:—
Hybrid Tea.

*Flower*

Blooming habit:—
*Recurrent.*—Continuous.
Bud:—
*Size.*—Very large.
*Form.*—Very long, pointed. Unaffected by hot or wet weather.
*Color.*—When sepals first divide—chestnut red. When half blown, inside of petals are carrot red and reverse of petals are chestnut red.
*Sepals.*—Serrated, stand up.
*Calyx.*—Shape, pear. Size, long. Aspect, smooth.
*Peduncle.*—Length, very long. Aspect, smooth. Color, light green. Strength, erect, slender.
*Opening.*—Bud opens well; unaffected by adverse conditions.
Bloom:—
*Size.*—Very large, 4 to 4½ inches when fully expanded.
*Borne.*—Singly and several together.
*Stems.*—Long, normal strength.
*Form.*—When first open—cupped. Permanence—outer petals curl back.
*Petalage.*—Double. Number of petals under normal conditions about 30.
*Color.*—Center of flower carrot red with orange suffusion. Outer petals same. Base of petals yellow. Inside of petals carrot red and orange. Reverse of petals brownish red. General tonality from a distance, orange scarlet.
*Discoloration.*—End of first day, orange scarlet. End of second day, carmine orange. End of third day, coral.
Petals:—
*Texture.*—Thick, unaffected by wet or hot weather.
*Appearance.*—Inside, satiny; outside, shiny.
*Form.*—Oval.
*Arrangement.*—Informal; petaloids in center, few, small.
*Persistence.*—Drop off cleanly.
*Fragrance.*—Moderate; nature—tea.
*Lasting quality.*—On the plant—very long. As cut flower—very long.
Genital organs:—
*Stamens, anthers.*—Large. Color, yellow. Arrangement, regular around styles.
*Stamens, filaments (threads).*—Long. Color, yellow.
*Pollen.*—Lemon yellow.
*Styles.*—Loosely separated, medium length, heavy.
*Stigmas.*—White.
Ovaries.—All enclosed in calyx.
Fruit:—
Variety is fertile with its own pollen.
*Form.*—Ovoid.
*Aspect.*—Smooth.
*Color at maturity.*—Orange.
*Sepals.*—Permanent; recurved.

*Plant*

Form:—
Bush.
Growth:—
Very vigorous, branching.
Foliage:—
Five, sometimes seven, leaflets.
*Size.*—Large.
*Quantity.*—Abundant.
*Color.*—New foliage: upper side, light green; under side, light green. Old foliage: upper side, normal green; under side, light green.
*Shape.*—Oval pointed.
*Texture.*—Upper side, glossy; under side, rough. Ribs and veins: ordinary.
*Edge.*—Serrated (saw toothed).
*Serration.*—Single; sharp.
*Leaf stem.*—Color, green. Under side, smooth.
*Stipules.*—Medium length; smooth.
*Disease resistance.*—Resistant.
Wood:—
*New wood.*—Color, light green; bark, smooth.
*Old wood.*—Color, green; bark, smooth.

Thorns:—(N. B. Thorns are divided into thorns, prickles and short needles.)
*Thorns.*—Quantity: on main stalks, ordinary; on laterals from stalk, few. Form: broad base; medium length; hooked downward. Color when young: red. Position: irregular.
*Prickles.*—Quantity: none on main stalks or laterals.
*Short needles.*—Quantity: none on main stalks or laterals.

I claim:—

A new variety of rose plant as disclosed, characterized by the distinct chestnut red color of its bud and half-open bloom gradually changing to carrot red with orange suffusion in the full blown flower and finishing satiny coral, substantially as shown and the profusion and continuity of its bloom.

JEAN H. NICOLAS.